(12) United States Patent
Qian

(10) Patent No.: US 6,924,325 B2
(45) Date of Patent: Aug. 2, 2005

(54) SILVER-CONTAINING DENTAL COMPOSITION

(75) Inventor: Xuejun Qian, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 405 days.

(21) Appl. No.: 10/177,055

(22) Filed: Jun. 21, 2002

(65) Prior Publication Data

US 2004/0002557 A1 Jan. 1, 2004

(51) Int. Cl.$^7$ .................. A61K 6/083; C08K 3/34; A61C 5/00
(52) U.S. Cl. .................. 523/113; 523/115; 523/116; 523/118; 524/443; 524/450; 433/228.1
(58) Field of Search ................. 523/113, 115, 523/116, 118; 524/443, 450; 433/228.1

(56) References Cited

U.S. PATENT DOCUMENTS

| | | | |
|---|---|---|---|
| 4,522,806 A | 6/1985 | Muhlemann et al. ......... 424/52 |
| 4,567,030 A | 1/1986 | Yuasa et al. ................. 423/326 |
| 4,775,585 A | 10/1988 | Hagiwara et al. .......... 428/323 |
| 4,820,507 A | 4/1989 | Klueppel et al. ............. 424/54 |
| 4,872,936 A | 10/1989 | Engelbrecht ............. 156/307.3 |
| 4,911,898 A | 3/1990 | Hagiwara et al. ........... 423/118 |
| 4,911,899 A | 3/1990 | Hagiwara et al. ........... 423/118 |
| 5,063,257 A | 11/1991 | Akahane et al. ............ 523/116 |
| 5,154,762 A | 10/1992 | Mitra et al. .................... 106/35 |
| 5,260,062 A | 11/1993 | Gaffar ........................ 424/401 |
| 5,330,746 A | 7/1994 | Friedman et al. ............. 424/49 |
| 5,338,773 A * | 8/1994 | Lu et al. ..................... 523/116 |
| 5,340,850 A | 8/1994 | Shimasue ................... 523/115 |
| 5,609,675 A | 3/1997 | Noritake et al. .............. 106/35 |
| 5,859,089 A | 1/1999 | Qian .......................... 523/116 |
| 6,127,451 A | 10/2000 | Qian .......................... 523/116 |
| 6,267,590 B1 | 7/2001 | Barry et al. .................... 433/8 |
| 6,326,417 B1 | 12/2001 | Jia .............................. 523/116 |
| 6,353,041 B1 | 3/2002 | Qian .......................... 523/116 |
| 6,355,704 B1 | 3/2002 | Nakatsuka et al. ......... 523/116 |
| 6,379,712 B1 | 4/2002 | Yan et al. .................... 424/618 |

FOREIGN PATENT DOCUMENTS

| | | | |
|---|---|---|---|
| JP | 63294607 | * 11/1988 |
| JP | 02142711 | 5/1990 |
| JP | 08119821 | 5/1996 |
| WO | WO 9907326 | 2/1999 |

OTHER PUBLICATIONS

European Patent Office, *Partial European Search Report*, for Application No. EP 03 25 3929, dated Oct. 17, 2003.
Wakasa et al., *Dental Application of silver zeolite. Dental restorative materials*, STN Chemical Abstracts, vol. 13, No. 127, Sep. 29, 1997, XP–002097679.

* cited by examiner

Primary Examiner—Tae H. Yoon
(74) Attorney, Agent, or Firm—Wood, Herron & Evans, L.L.P.

(57) ABSTRACT

A dental composition comprising a silver-containing ceramic having antimicrobial and color stabilizing properties and methods for using the composition. The composition comprises a silver-containing glass powder or a silver-containing zeolite powder, at least one monomer having at least one ethylenically unsaturated group, and a polymerization initiator system. Other components, such as a filler, may also be included. The inventive composition possesses antimicrobial properties and exhibits excellent mechanical properties upon curing. Additionally, when the polymerization initiator is a two-part redox initiator system, the composition has improved color stability. The inventive composition can be used as a dental restorative composition, an endodontic composition, an orthodontic composition, and/or a prosthetic composition.

16 Claims, No Drawings

SILVER-CONTAINING DENTAL COMPOSITION

FIELD OF THE INVENTION

This invention relates to a dental composition comprising a silver-containing ceramic that exhibits antimicrobial properties and improved color stability without compromising mechanical properties.

BACKGROUND OF THE INVENTION

Resin based dental restorative materials are becoming the material of choice by dentists and patients due to their desirable aesthetic properties. However, gap formation occurs between the restorative material and tooth structure as a result of inadequate adhesive bonding, polymerization shrinkage stress, thermal stress, and mechanical stress (mastication force). This leads to microleakage and, subsequently, secondary caries.

A restorative material that possesses antibacterial properties and inhibits bacterial growth around the restoration would be desirable. Various antibacterial agents have been incorporated into oral products such as rinse solutions, toothpastes, coatings, and dental restorative compositions to kill bacteria or inhibit bacterial growth. Those antibacterial agents include phenols/essential oils (U.S. Pat. Nos. 5,260,062 and 6,326,417), quaternary ammonium compounds (U.S. Pat. Nos. 4,820,507; 5,330,746; and 6,355,704), and metal salts containing zinc (U.S. Pat. No. 4,522,806).

Silver has been shown to be an effective antibacterial agent. For example, U.S. Pat. No. 5,340,850 discloses a method to physically implant silver ions onto the surface of an inorganic filler or into a resin matrix using a special ion implantation apparatus. U.S. Pat. No. 6,379,712 discloses a nanosilver-containing antibacterial granule comprising a metallic silver core surrounded by silver oxide, obtained by precipitating silver from solution onto cut stalk marrow, and grinding the nanosilver-containing stalk marrow. U.S. Pat. No. 6,267,590 discloses an orthodontic dental bracket and arch wire coated with an antimicrobial polymeric coating composition comprising a zeolite particle containing silver ions. U.S. Pat. No. 4,911,898 discloses preparation of zeolite particles containing silver ions having antibacterial properties, prepared by doping the zeolite particle with silver ions through ion-exchange in a silver-ion-containing aqueous solution.

None of the aforementioned references disclose a dental composition containing ethylenically unsaturated monomers and polymerization initiators in which a silver-containing ceramic provides desirable properties, such as antimicrobial properties and color stabilization, without sacrificing the mechanical strength of the dental composition.

SUMMARY OF THE INVENTION

One embodiment of the invention is directed to an antimicrobial dental composition comprising a silver-containing ceramic, at least one monomer having at least one ethylenically unsaturated group, and a polymerization initiator system. The composition may contain other components such as a filler, a stabilizer, an ultraviolet light absorber, a colorant, solvents to modify its viscosity, etc. The silver containing ceramic is either a glass powder or a zeolite powder; in one embodiment it is present at a concentration in the range of about 0.0%$^{w/w}$ to about 10%$^{w/w}$ of the composition, and in another embodiment it is present in the range of about 0.05%$^{w/w}$ to about 5%$^{w/w}$ of the composition. In one embodiment the powder mean particle size is less than about 30 μm, and in another embodiment the powder mean particle size is less than about 5 μm. The glass powder may be silveraluminophosphate glass or silveraluminosilicate glass. The zeolite powder may be aluminosilicate zeolite with silver ions at its ion-exchangeable sites. The silver containing ceramic may also include other elements, such as copper and zinc. The ethylenically unsaturated group in the composition may be a vinyl group, a methacrylate group, and/or an acrylate group. The polymerization initiator system in the composition may be a photo-, redox-, and/or a thermal initiator system. The composition may be a resin composite, a resin-ionomer, and/or a resin-modified glass-ionomer.

Another embodiment of the invention is directed to a color-stabilized two-part (catalyst part and base part) dental composition comprising a silver-containing ceramic, at least one monomer having at least one ethylenically unsaturated group, and a redox polymerization initiator system with each part containing one component of the redox initiator system. The catalyst part containing the oxidizing agent of the redox initiator system, such as a peroxide, exhibits improved shelf color stability when a silver-containing ceramic is incorporated. The composition may optionally contain a filler.

Another embodiment of the invention is a method of providing an antimicrobial composition to a tooth. A composition of a silver-containing ceramic antimicrobial, at least one monomer having at least one ethylenically unsaturated group, and a polymerization initiator system is prepared. The composition may optionally contain a filler. The composition may be provided to the tooth and then cured, or may be cured and then provided to the tooth. The composition may be used as a dental restorative composition, an endodontic composition to seal and/or fill a root canal, an othodontic composition, or a prosthetic composition.

These and other embodiments of the inventive composition will be apparent in light of the following detailed description and examples.

DETAILED DESCRIPTION OF THE INVENTION

The inventive composition comprises a silver-containing ceramic, one or more monomers having at least one ethylenically unsaturated functional group, and a polymerization or curing initiator system. The silver-containing ceramic, providing an antimicrobial effect, may be either a silver-containing glass powder or a silver-containing zeolite powder, and may contain additional antimicrobial agents such as zinc and/or copper. Other components may also be included, such as a filler, a colorant, a stabilizer to improve the shelf-life of the composition, a stabilizer against the effects of ultraviolet (UV) light, etc.

The silver-containing ceramic provides a sustained release of active components, i.e. silver, into an oral environment surrounding a restoration, and helps to prevent secondary caries adjacent to the restoration where gaps develop between the restoration and the tooth structure. When incorporated into dental restorative compositions, the mechanical strength, optical properties, and shelf-stability of the resulting material was not compromised.

The silver-containing ceramic and at least one monomer having at least one ethylenically unsaturated group may be used in a two-part dental composition containing a redox polymerization initiator. The two parts are the catalyst part and the base part, with each part containing one component of the redox initiator system. The base part usually contains the reducing agent of the redox initiator system, while the catalyst part contains the oxidizing agent of the redox initiator system. The composition is cured when the catalyst part is mixed with the base part, initiating free radical polymerization, and the composition is said to be a self-cure composition (without external activation source such as light or heat). A photo-initiator can be optionally incorporated in the base part of the composition to obtain a dual-cure (self-cure and light-cure) two-part composition. It was know to dental manufacturers and dental practitioners that the catalyst part containing the oxidizing agent generally had a limited color stability and became discolored after storage for about six months. However, when the silver-containing ceramic was incorporated into the composition, the catalyst part exhibited significantly improved color stability, providing a two-part dental composition of more consistent color.

The silver-containing ceramic is a silver-containing glass powder or a silver-containing zeolite powder. In one embodiment, the powders have a mean particle size of less than 30 µm. In another embodiment, the powders have a mean particle size less than 5 µm. The silver-containing glass can be silveraluminophosphate glass or silveraluminosilicate glass. The glass may also contain other antibacterial elements, such as zinc and/or copper, to enhance the antimicrobial effect. During the glass making process, additional elements may be introduced for ease of manufacture, for imparting radiopacity to the dental composition, for release of fluoride, etc. Examples of such elements include boron, phosphor, fluorine, calcium, barium, strontium, or other alkali/alkaline metal elements. The silver is incorporated into the glass by melting together the silver-containing compound with other glass forming ingredients during manufacture of the glass. One silver-containing glass antimicrobial additive is Irgaguard® B7000 (Ciba Specialty Chemicals Corporation, Tarrytown N.Y.). Irgaguard® B7000 is a mixture of silver-zinc glass fine powder and barium sulfate fine powder, with a mean particle size of 1.8 µm.

The silver-containing zeolite powder can be prepared by replacing some or all of the ion-exchangeable metal ions, usually alkali or alkaline metal ions, of zeolite particles with silver ions through an ion-exchange process in an aqueous solution containing silver ions. Antibacterial zeolites and their preparation are disclosed in U.S. Pat. Nos. 4,911,899 and 4,775,585, each of which is expressly incorporated by reference herein in its entirety. Either natural or synthetic zeolite may be used. Zeolite is generally aluminosilicate having a three-dimensional grown skeleton structure generally expressed by $xM_{2/n}O \cdot Al_2O_3 \cdot ySiO_2 \cdot zH_2O$ where M represent an ion-exchangeable metal (alkali or alkaline) ion; n represent the valence of the metal; x is the molar coefficient of the metal oxide in relation to $Al_2O_3$; and y is the molar coefficient of silica in relation to $Al_2O_3$; z is the number of water of crystallization. Zeolites include A zeolite, Z zeolite, Y zeolite, and mordenite. Other antimicrobial metal ions such as zinc and copper ions, in addition to silver ions, can also be incorporated by the ion-exchange process. In one embodiment, silver-zinc zeolite is used where silver ions and zinc ions are incorporated onto the ion-exchangeable sites of the zeolite through an ion-exchange process. One silver-zinc zeolite is Irgaguard® B5000 (Ciba Specialty Chemicals Corporation, Tarrytown N.Y.). Irgaguard® B5000 has a mean particle size of 0.3 µm.

The concentration range for the silver-containing ceramic ranges from about $0.01\%^{w/w}$ to about $10\%^{w/w}$ of the composition. In one embodiment, the concentration range is from about $0.05\%^{w/w}$ to about $5.0\%^{w/w}$ of the composition.

Any monomers having at least one ethylenically unsaturated group may be used. Examples of ethylenically unsaturated groups include vinyl, acrylate, and methacrylate groups. Examples of monomers include, but not limited to, the following, where (meth)acrylate denotes acrylate or methacrylate: hydroxyethyl (meth)acrylate, hydroxypropyl (meth)acrylate, hydroxybutyl (meth)acrylate; glycerol di(meth)acrylate, glycerol mono(meth)acrylate, methyl (meth)acrylate, ethyl (meth)acrylate, propyl (meth)acrylate, butyl (meth)acrylate, hexyl (meth)acrylate, octyl (meth) acrylate, lauryl (meth)acrylate, decyl (meth)acrylate, tridecyl (meth)acrylate; 2-ethoxyethyl (meth)acrylate, 2'-ethoxy-2-ethoxyethyl (meth)acrylate, ethyleneglycol di(meth) acrylate, diethyleneglycol di(meth)acrylate, triethyleneglycol di(meth)acrylate, tetraethyleneglycol di(meth)acrylate, polyethyleneglycol mono-(meth)acrylate, polyethyleneglycol di-(meth)acrylate, polypropyleneglycol mono-(meth)acrylate, polypropyleneglycol di-(meth) acrylate, polytetramethyleneglycol mono-(meth)acrylate, polytetramethyleneglycol di-(meth)acrylate, hexanediol di(meth)acrylate, trimethyloylpropane tri(meth)acrylate, UDMA (reaction product of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylated bisphenol A dimethacrylate (EBPADMA-n, n is the total number of moles of ethylene oxide in the molecule; in one embodiment n is 2–20 units), tetrahydrofurfuryl (meth)acrylate, or a mixture thereof. In various embodiments, the monomers contain more than one ethylenically unsaturated group per molecule.

The free-radical polymerization initiator may be any initiator that can initiate free radical polymerization of monomers with an ethylenically unsaturated group, and may be one or more photo-initiator(s), redox initiator(s), and/or heat (thermal) initiator(s). Examples of photo-initiators include benzoin, benzoin ethers and esters, 2,2-diethoxy acetophenone, diketone compounds, bisacylphosphine oxide, diaryliodonium salt, and/or triarylsulfonium salt. Additionally, an activator such as a tertiary amine can be used with the photo-initiators to enhance curing efficiency. Photo-initiator systems may include camphoroquinone and a tertiary amine such as ethyl 4-(N,N-dimethylamino) benzoate, 2-(ethylhexyl)-4-(N,N-dimethylamino) benzoate, and N,N-dimethylaminoethyl methacrylate. A redox initiator system has at least one reducing agent and at least one oxidizing agent. The reducing agent may be a tertiary amine or an organic compound containing the —$SO_2M$ (where M is H or alkali metal ion) group. In various embodiments, the reducing agent may be N,N-dihydroxyethyl p-toluidine, N,N-dimethyl p-toluidine, N,N-dimethylaminophenylethyl alcohol, N,N-dimethylaminophenylacetic acid, benzenesulfinic acid, toluenesulfinic acid, sodium benzenesulfinate, potassium benzenesulfinate, sodium toluenesulfinate, potassium toluenesulfinate. The oxidizing agent may be a peroxide, such as benzoyl peroxide, hydrogen peroxide, di-t-butyl peroxide, t-butyl hydrogen peroxide. A heat initiator may be a peroxide, persulfate, or azo compound, such as benzoyl peroxide, potassium persulfate, 2,2'-azo-bis (isobutyronitrile), and 1,1'-azo-di-(hexahydrobenzonitrile).

The photo-initiator, redox initiator, and heat initiator can be used alone or in combination. A heat initiator may be used in a single part, heat-cure only system such as in an inlay, onlay, or crown composition. A photo-initiator may be used in a single part, light-cure only system, such as in a light-cure composite filling material or light-cure veneer cement. The redox initiator may be used in a two-part self-cure (i.e. curing without the activation of light or heat) composition with each part containing one component (either the oxidizing agent or the reducing agent) of the redox initiator system. The photo-initiator can be used in combination with the redox initiator system to make the system dual-cure, i.e. both light-cure and self-cure. The heat-cure initiator and photo-initiator can be used together in a single part dual-cure system, i.e. both light-cure and heat-cure. The concentration of the initiator(s) is in the range of about $0.01\%^{w/w}$ to about $5.0\%^{w/w}$. In one embodiment, the concentration of the initiator(s) is in the range of about $0.05\%^{w/w}$ to about $3.0\%^{w/w}$.

A filler is optional, depending upon the application. While most compositions require the use of a filler, a primer or an adhesive composition may not contain a filler. A filler may be used to enhance mechanical properties, reduce polymerization shrinkage, improve Theological properties, and increase radiopacity of the composition for easy detection of gaps or voids. Examples of fillers include inorganic metal, salt, oxide, silicate, aluminosilicate, aluminoborosilicate, fluoroaluminosilicate, colloidal silica, precipitated silica, polymeric filler, and/or polymerized composite filler with reinforcing inorganic particles. Inorganic fillers for increased x-ray contrast include metals, silicates, aluminosilicates, salts and oxides containing elements of high atomic number including strontium, bismuth, tungsten, barium, yterbium, ytrium etc. Examples include barium sulfate, silver, strontium fluoride, barium fluoride, yterbium fluoride, ytrium fluoride, barium tungstate, zinc oxide, zirconia, bismuth(III) oxide, bariumaluminosilicate, bariumaluminoborosilicate, strontiumaluminosilicate, bariumaluminofluorosilicate, strontiumaluminofluorosilicate, zincaluminosilicate, zirconiumaluminosilicate, etc. Fumed silica, colloidal silica, or precipitated silica can also be incorporated to improve the dispersion of the filler, as well as the rheological and handling properties of the material. Examples of colloidal silicas are "Aerosil" series "OX-50", "OX-130", and "OX-200" silica sold by Degussa (Ridgefield Park N.J.), "Cab-O-Sil M5" and "Cab-O-Sil TS-530" silica sold by Cabot Corporation (Tuscola Ill.). The fillers also include nanoparticles fillers such as those obtained through sol-gel process as disclosed in U.S. Pat. Nos. 4,567,030 and 5,609,675, the disclosure of each is expressly incorporated by reference herein in its entirety. Mixtures of different fillers can be used.

For inorganic fillers, the surface of the filler may be treated or coated with a coupling agent such as gamma-methacryloyloxypropyltrimethoxysilane (A-174). A coupling agent enhances the interfacial bonding between the filler and resin matrix, and improves mechanical properties of the composition. Mean particle sizes of the filler are less than 20 $\mu$m, and in one embodiment are less than 5 $\mu$m. The concentration range of total filler(s) is 0% up to about 95% by weight, depending on the application. For primer or adhesive applications, the concentration range is 0% up to about 60%. For cement applications, the concentration range is about 20% up to about 75%. For filling materials, the concentration range is about 30% up to about 95%.

Other components may be incorporated in the inventive composition, including colorants, stabilizers, UV absorbers, and other antimicrobials. Colorants are used to achieve a desired shade, and may be inorganic pigments or organic dyes. Stabilizers are polymerization inhibitors to improve the shelf stability of the composition. Most commonly used stabilizers include 2,6-di-(tert-butyl)-4-methylphenol (BHT) and 4-methoxyphenol (MEHQ). UV absorbers are used to improve the color stability of the restorative material upon exposure to UV light. An example of UV absorber is 2-hydroxy4-methoxybenzophenone (UV-9).

The inventive compositions may be used as a dental restorative composition, an endodontic composition, an orthodontic composition, or a prosthetic composition. A restorative composition may be a dental filling material, a dental cement, a dental liner, a dental base, a dental primer, a dental adhesive, or a dental pit/fissure sealant composition. An endodontic composition may be an endodontic sealing and/or filling material for sealing and/or filling of a root canal. These may be of the type disclosed in U.S. Pat. No. 6,353,041 and co-pending application Ser. No. 09/657,961, each of which is expressly incorporated by reference herein in its entirety. An orthodontic composition may be an orthodontic primer, adhesive, or cement composition for adhering an orthodontic appliance to a tooth surface. A prosthetic composition may include a dental inlay, onlay, crown, bridge, or a denture composition.

The composition may be a purely resin-based composite, or may be a hybrid material such as a resin-ionomer (RI) or resin-modified glass-ionomer (RMGI),as disclosed in U.S. Pat. Nos. 5,859,089; 6,127,451; 4,872,936; 5,063,257; 5,154,762, each of which is expressly incorporated by reference herein in its entirety. RMGI is a hybrid material that contains at least an acidic monomer or polymer, water, a monomer with at least one ethylenically unsaturated group, an ion-leachable filler that can undergo a setting reaction with the acidic monomer or polymer, and a polymerization initiator. The acidic monomer or polymer preferably contains at leastone ethylenically unsaturated group. The polymerization initiator can be a photo-initiator, a redox initiator, or a combination of both. A resin-ionomer material, also called a compomer, contains at least an acidic monomer with at least one ethylenically unsaturated group, at least one co-monomer with at least one ethylenically unsaturated group, an ion-leachable filler, and a polymerization initiator. A resin-ionomer does not contain water as an intentionally added component.

The inventive composition may also incorporate a solvent, which may be used to modify the viscosity of the composition. In one embodiment, the solvent is added when a primer, an adhesive, or cement composition is formulated. Solvents include water, methanol, ethanol, isopropanol, acetone, and methyl ethyl ketone (MEK).

The inventive composition is applied to the tooth or tooth structure, then is hardened or cured (intra-oral curing) through free radical polymerization. If the composition is used as a permanent prosthetic such as a crown/bridge or denture material, the composition is cured extra-orally through free radical polymerization by light, heat, and/or a redox initiator system, and is then adhered to the prepared dentition using an adhesive and/or a cement.

EXAMPLES

The following examples illustrate how the composition is applied and do not limit the scope of the invention.

Bacterial Growth Inhibition Test

A bacteria growth inhibition test against *Streptococcus mutans* was conducted according to American Association of Textile Chemist and Colorist (AATCC) Test Method 100. Cured specimens of 38 mm×38 mm square plate with a thickness of 0.4 mm were prepared and inoculated with ~$2\times10^5$ CFU (colony forming unit) of *Streptococcus mutans*. Plate counts were performed at the time of inoculation (0 time) and after 24 hours of incubation at 37° C. The percent of bacterial reduction was determined from the counts taken at 0 time and after 24 hours incubation.

Compressive Strength (CS) Test

The specimens were prepared by condensing the paste into a stainless-steel mold with a dimension of 4 mm (diameter)×3 mm (height), and then photo-curing the paste with a Demetron Optilux 401 curing light (Kerr Corporation, Orange Calif.) for 30 seconds from each side. The cured disk was removed from the mold and conditioned in 37° C. water for 24 hours before subjecting to mechanical testing on an Instron Universal Tester (Model 4202) in compression mode with a crosshead speed of 0.50 mm/minute. The peak load at which the specimen broke was used to calculate the compressive strength and was expressed in MPa unit. Six specimens were tested for each formula.

Diametral Tensile Strength (DTS) Test

The specimens were prepared by condensing the paste into a stainless-steel mold with a dimension of 6 mm (diameter)×3 mm (height), and then photo-curing the paste with a Demetron Optilux 401 curing light (Kerr Corporation, Orange Calif.) for 30 seconds from each side. The cured disk was removed from the mold and conditioned in 37° C. water for 24 hours before subjecting to mechanical testing on an Instron Universal Tester (Model 4202) in compression mode with a crosshead speed of 10 mm/minute. The load was applied in the diameter direction in compression mode. The peak load at which the specimen broke was used to calculate the compressive strength and was expressed in MPa units. Six specimens were tested for each formula.

Flexural Strength (FS) and Young's Modulus (E) Tests

FS and E were measured from the same flexural test according to ISO 4049 standard as known to one skilled in the art. The specimens were prepared by condensing the paste into a stainless-steel mold with a dimension of 2 mm×2 mm×25 mm, and then photo-cured from both sides. The cured disk was removed from the mold and conditioned in 37° C. water for 24 hours before subjecting to mechanical testing on an Instron Universal Tester (Model 4202) in three-point bending mode with a crosshead speed of 0.5 mm/minute. The peak load at which the specimen broke was used to calculate the FS and was expressed in MPa units. E was obtained from the slope of stress-strain curve in the initial linear region. Six specimens were tested for each formula.

Color Measurement

Color measurement was conducted using a portable spectrophotometer (Model SP60, X-Rite Inc.) in reflectance mode against the white background of an opacity card (Form 2A, Leneta Co.). The color is expressed as L*a*b* using the CIELAB scale where L* defines the lightness, a* denotes the red/green value, and b* denotes the yellow/blue value. For color measurement, 1 mm thick specimens were used.

EXAMPLE 1

Three pastes (A, B and C) were made based on Nexus™ 2 base clear paste (Kerr Corporation, Orange Calif.). Bacterial growth inhibition tests according to the AATCC 100 method were conducted on the three compositions. Paste A was same as Nexus™ 2 base clear shade composition and served as the control, paste B was made by incorporating 3.0% Irgaguard® B7000 (an antimicrobial silver-zinc glass powder from Ciba Specialty Chemicals Corporation, Tarrytown N.Y.) into Nexus™ 2 base clear shade composition, and paste C was made by incorporating 0.4% Irgaguard® B5000 (an antimicrobial silver-zinc zeolite from Ciba Specialty Chemicals Corporation) into Nexus™ 2 base clear composition. The specimens for the bacterial inhibition test were prepared according to above described method and the curing of the specimen was achieved by light-curing the specimen for one minute.

The results of the bacterial growth inhibition test against *Streptococcus mutans* are shown in Table 1. While Paste A (Nexus™ 2 base clear, control) did not inhibit bacterial growth, Paste B (Nexus™ 2 base clear containing 3.0% Irgaguard® B7000) reduced the bacterial count by 99.11%, and Paste C (Nexus™ 2 clear containing 0.4% Irgaguard® B5000) reduced the bacterial count by more than 99.95%.

TABLE 1

Bacterial Growth Inhibition of Silver-Containing Additives Against S. mutans (AATCC100 Method)

| Formula | Composition | CFU (Colony Forming Units) | | Percent Reduction (%) |
|---|---|---|---|---|
| | | Initial | 24 hour contact | |
| Paste A | Nexus ™ 2 Base Clear | 210000 | 550000 | No reduction (increased) |
| Paste B | Nexus ™ 2 Base Clear with 3.0% Irgaguard ® B7000 | 180000 | 1600 | 99.11% |
| Paste C | Nexus ™ 2 Base Clear with 0.4% Irgaguard ® B5000 | 190000 | <100 | >99.95% |

EXAMPLE 2

Irgaguard® B7000 was incorporated in the catalyst paste of a commercial core buildup material (CoreRestore® 2, Kerr Corporation, Orange Calif.) at $3\%^{w/w}$ concentration. The color stability of the catalyst pastes with and without Irgaguard® B7000 was measured initially and then at different time intervals after the pastes were stored at elevated temperatures (37° C. and 42° C.). The results are shown in Table 2.

A CoreRestore® 2 catalyst paste without Irgaguard® B7000 became significantly more yellow (b* value becoming more positive) and somewhat more green (a* value becoming more negative) than CoreRestore® 2 catalyst paste with Irgaguard® B7000.

The overall color change was calculated using following equation:

$$\Delta E = \{(L^*_1 - L^*_0)^2 + (a^*_1 - a^*_0)^2 + (b^*_1 - b^*_0)^2\}^{1/2}$$

Where $L^*_0$, $a^*_0$, and $b^*_0$ were the initial color coordinates of freshly prepared material before aging; and $L^*_1$, $a^*_1$, and $b^*_1$, were the color coordinates after aging.

TABLE 2

Effect of B7000 Additive on Color Stability of CoreRestore ® 2 Catalyst Paste

| Storage Temp. | Storage Time | CoreRestore ® 2 | | | | CoreRestore ® 2 with 3% Irgaguard ® B7000 | | | |
|---|---|---|---|---|---|---|---|---|---|
| | | L* | a* | b* | ΔE | L* | a* | b* | ΔE |
| 37° C. | Initial | 74.84 | −1.79 | 4.41 | | 74.56 | −1.72 | 4.22 | |
| | 11 days | 74.43 | −2.10 | 6.80 | 2.44 | 74.35 | −1.81 | 4.80 | 0.62 |
| | 18 days | 74.10 | −2.18 | 6.97 | 2.69 | 74.43 | −1.98 | 4.91 | 0.75 |
| | 25 days | 73.49 | −2.62 | 9.60 | 5.43 | 73.84 | −1.96 | 5.70 | 1.66 |
| | 32 days | 73.16 | −3.42 | 12.35 | 8.28 | 73.95 | −2.09 | 6.10 | 2.01 |
| | 39 days | 73.27 | −3.67 | 13.25 | 9.17 | 74.22 | −2.36 | 6.85 | 2.73 |
| 42° C. | 4 days | 74.39 | −1.90 | 5.24 | 0.95 | 74.47 | −1.80 | 4.46 | 0.27 |
| | 8 days | 74.08 | −2.14 | 6.49 | 2.24 | 74.46 | −1.84 | 4.77 | 0.57 |
| | 11 days | 73.76 | −2.22 | 7.42 | 3.23 | 74.37 | −1.89 | 5.01 | 0.83 |
| | 14 days | 73.33 | −2.67 | 9.43 | 5.32 | 74.01 | −1.93 | 5.09 | 1.05 |

The color change (ΔE) for the CoreRestore® 2 catalyst paste with the silver-zinc glass additive (Irgaguard® B7000) was much less than that for the CoreRestore® 2 catalyst paste without Irgaguard® B7000. Therefore CoreRestore® 2 catalyst paste with the silver-zinc glass additive was much more color stable than CoreRestore® 2 catalyst paste without the additive.

EXAMPLE 3

Irgaguard® B7000 was incorporated in the catalyst paste of a commercial resin cement (Nexus™ 2 Kerr Corporation, Orange Calif.) at $3\%^{w/w}$ concentration. The color stability of the pastes with and without Irgaguard® B7000 was measured initially and then after aging at 42° C. for twenty-two days.

The results are shown in Table 3. Nexus™ 2 catalyst paste without Irgaguard® B7000 became significantly more yellow (b* value becoming more positive) and somewhat more green (a* value becoming more negative) than Nexus™ 2 catalyst paste with Irgaguard® B7000. The color change (ΔE) for the Nexus™ 2 catalyst paste with Irgaguard® B7000 was much less than that for the Nexus™ 2 catalyst paste without Irgaguard® B7000. Therefore Nexus™ 2 catalyst paste with the silver-zinc glass additive was much more color stable than Nexus™ 2 catalyst paste without the additive.

TABLE 3

Color stability of Nexus ™ 2 Catalyst Pastes

| Storage Temp. | Storage Time | Nexus ™ 2 | | | | Nexus ™ 2 with 3% Irgaguard ® B7000 | | | |
|---|---|---|---|---|---|---|---|---|---|
| | | L* | a* | b* | ΔE | L* | a* | b* | ΔE |
| | Initial | 72.01 | −1.88 | 5.06 | | 71.86 | −1.90 | 4.92 | |
| 42° C. | 22 days | 71.07 | −3.57 | 11.05 | 6.29 | 71.89 | −2.75 | 7.98 | 3.18 |

EXAMPLE 4

Irgaguard® B7000 $3\%^{w/w}$ was introduced into Nexus™ 2 base clear paste. The mechanical properties (compressive strength, diametral tensile strength, and flexural strength) were tested according to the procedures mentioned above, and the specimens were light-cured with a Demetron Optilux 401 curing light (Kerr Corporation, Orange Calif.) from each side. The results are listed in Table 4.

TABLE 4

The Effect of B7000 Additive on Mechanical Properties of Nexus ™ 2 Base Paste

| Mechanical Properties | Nexus ™ 2 | Nexus ™ 2 with 3% Irgaguard ® B7000 |
|---|---|---|
| Compressive Strength, MPa | 374 ± 12 | 395 ± 24 |
| Diametral Tensile Strength, MPa | 56.6 ± 4.6 | 55.3 ± 5.2 |
| Flexural Strength, MPa | 156 ± 7 | 154 ± 6 |

There are no statistically significant differences between the mechanical properties Nexus™ 2 base clear paste and Nexus™ 2 base clear paste with $_3\%^{w/w}$ Irgaguard® B7000. Therefore, incorporating a silver-zinc glass additive into the Nexus™ 2 base paste did not adversely affect its mechanical properties.

EXAMPLE 5

Irgaguard® B7000 ($3\%^{w/w}$) was introduced into a resin composite filling material, Prodigy™ (Kerr Corporation, Orange Calif.) which is a light-curable single-part paste. The mechanical properties were tested and the specimens were light-cured with a Demetron Optilux 401 curing light (Kerr Corporation, Orange Calif.) for 30 seconds from each side. The results are shown in Table 5.

TABLE 5

The Effect of Irgaguard ® B7000 Additive on Mechanical Properties of Prodigy ™

| Mechanical Properties | Prodigy ™ | Prodigy ™ with 3% Irgaguard ® B7000 |
|---|---|---|
| Compressive Strength, MPa | 418 ± 20 | 405 ± 16 |
| Diametral Tensile Strength, MPa | 62.1 ± 6.9 | 66.9 ± 3.9 |
| Flexural Strength, MPa | 138 ± 10 | 140 ± 11 |

There are no statistically significant differences between the mechanical properties of Prodigy™ and Prodigy™ with $3\%^{w/w}$ Irgaguard® B7000. Therefore, a incorporating silver-zinc glass additive into the Prodigy™ paste did not adversely affect its mechanical properties.

The above examples demonstrated the usefulness of silver-containing glass or zeolite ceramics in resin-based dental restorative materials. While imparting excellent antibacterial properties, they also greatly improved the color stability of the catalyst paste of any two-part system with no negative effect on the mechanical properties of the material.

The silver-containing glass or zeolite ceramic can also be incorporated into other dental restorative, endodontic, orthodontic, and prosthetic compositions. The use for the material incorporating the antibacterial additives can be temporary (last less than three months) or permanent (last more than three months). Orthodontic adhesives or cements incorporating silver-containing glass or zeolite can be especially useful for orthodontic applications where good oral hygiene may be difficult to maintain and bacterial growth is more difficult to control. The antibacterial additives can be incorporated into a single-part dental restorative material, such as a light-curable material (with a light-cure initiator), or heat-curable material (with a heat-cure initiator), or a combination of heat- and light-curable material. The light-curable material can be a composite filling material, a cement, a pit/fissure sealant, a base, or a liner. The heat-curable material can be a prosthetic material such as an inlay, an onlay, or a crown material that is polymerized extra-orally by heat or a combination of light and heat, and then adhered to the tooth structure with an adhesive and/or a cement. The antibacterial additives can also be incorporated into a two-part dental material such as a self-curable (with a redox initiator system) or dual-curable (combination of self-cure and heat-cure, or combination of light-cure and self-cure) material. Overall any configurations (such as light-cure versus self-cure or dual-cure; one-part versus two-part; filling material versus cement, liner, or adhesive, or endodontic sealing material; composite resin versus hybrid material such as resin-ionomer or resin-modified glass-ionomer) can be easily obtained by incorporating different curing initiators (photo-initiator, heat-cure initiator, redox initiator, or a combination thereof), filler type (reactive filler and/or non-reactive filler), and modifying viscosity (varying filler concentration, and/or use of solvent).

The above examples are for illustrations only, and should not be construed to limit the scope of this invention. It should be understood that the embodiments of the invention shown and described in the specification are only preferred embodiments of the inventor who is skilled in the art and are not limiting. Therefore, various changes, modifications or alterations may be made or resorted to without departing from the spirit of the invention and the scope of the following claims.

What is claimed is:

1. A dental composition comprising
   a silver-zinc containing glass,
   at least one monomer having at least one ethylenically unsaturated group,
   a polymerization initiator system and
   optionally a finely divided filler.

2. The composition of claim 1 wherein in the filler is selected from the group consisting of inorganic metal, salt, oxide, silicate, aluminosilicate, aluminoborosilicate, fluoroaluminosilicate, colloidal silica, precipitated silica, polymeric filler, polymerized composite filler with inorganic particles, bariumaluminosilicate, bariumaluminoborosilicate, strontiumaluminosilicate, zincaluminosilicate, bariumaluminofluorosilicate, strontiumaluminofluorosilicate, zirconia, zirconiumaluminosilicate, fumed silica, and combinations thereof.

3. The composition of claim 1 wherein silver-zinc containing glass is at a concentration in the range of about $0.01^{w/w}$ to about $10\%^{w/w}$ of the composition.

4. The composition of claim 1 wherein the silver-zinc containing glass is a powder.

5. The composition of claim 4 wherein the sliver-zinc containing glass powder is made by melting the silver compound with a plurality of glass-forming ingredients and then forming the glass into a powder.

6. The composition of claim 4 wherein the silver-zinc containing glass powder is selected from the group consisting of silveraluminophosphate glass and silveraluminosilicate glass.

7. The composition of claim 1 wherein the ethylenically unsaturated group is selected from the group consisting of a vinyl group, a methacrylate group, an acrylate group, and combinations thereof.

8. The composition of claim 1 wherein the polymerization initiator system is selected from the group consisting of a photo-initiator system, a redox initiator system, a heat initiator system, and combinations thereof.

9. The composition of claim 1 further comprising component selected from the group consisting of a solvent, a colorant, a stabilizer, an ultraviolet light absorber, and combinations thereof.

10. The composition of claim 1 wherein the composition is selected from the group consisting of a resin composite, a resin-ionomer, and a resin-modified glass-ionomer.

11. A color-stabilized dental a composition comprising a silver-zinc containing glass, at least one monomer having at least one ethylenically unsaturated group, and a peroxide initiator.

12. The composition of claim 11 further comprising a filler.

13. The composition of claim 11 wherein the peroxide initiator is used to cure the composition by thermal activation.

14. The composition of claim 11 wherein the peroxide initiator is used to cure the composition by mixing with a second composition comprising a reducing agent.

15. A method for providing an antimicrobial composition to a tooth comprising preparing a composition of claim 1 providing the composition to the tooth, and curing the composition.

16. The method of claim 15 wherein the composition is selected from the group consisting of a filling material, a cement, a liner, a base, a primer, an adhesive, a sealant, an endodontic sealer, an endodontic filler, and combinations thereof.

* * * * *

UNITED STATES PATENT AND TRADEMARK OFFICE
CERTIFICATE OF CORRECTION

PATENT NO.    : 6,924,325 B2
DATED         : August 2, 2005
INVENTOR(S)   : Qian It is certified that error appears in the above-identified patent and that said Letters Patent is hereby corrected as shown below:

Column 1,
Line 66, "...range of about 0.0%$^{w/w}$ to about..." should be -- ...range of about 0.01%$^{w/w}$ to about.... --.

Column 5,
Line 15, "...improve Theological properties..." should be -- ...improve theological properties... --.
Line 67, "2-hydroxy4-..." should be -- 2-hydroxy-4-... --.

Column 6,
Line 29, "...contains at leastone..." should be -- ...contains at least one... --.

Column 10,
Line 22, "...mechanical properties Nexus$^{TM}$ 2 base..." should be -- ...mechanical properties of Nexus$^{TM}$ 2 base... --.
Line 24, "...clear paste with $_3$%$^{w/w}$ ..." should be -- ...clear paste with 3%$^{w/w}$ ... --.

Column 11,
Line 54, "...wherein in the filler is..." should be -- ...wherein the filler is... --.

Column 12,
Line 13, "...wherein the sliver-zinc..." should be -- ...wherein the silver-zinc... --.
Line 27, "...further comprising component selected from..." should be -- ...further comprising a component selected from... --.
Line 36, "...dental a composition comprising a..." should be-- ...dental composition comprising a... --.

UNITED STATES PATENT AND TRADEMARK OFFICE
CERTIFICATE OF CORRECTION

PATENT NO. : 6,924,325 B2
DATED : August 2, 2005
INVENTOR(S) : Qian

It is certified that error appears in the above-identified patent and that said Letters Patent is hereby corrected as shown below:

<u>Column 12 (cont'd),</u>
Line 49, "... a composition of claim 1 providing..." should be -- ...a composition of claim 1, providing... --.

Signed and Sealed this

Twenty-eighth Day of March, 2006

JON W. DUDAS
*Director of the United States Patent and Trademark Office*